United States Patent [19]

Butters et al.

[11] Patent Number: 4,754,080

[45] Date of Patent: Jun. 28, 1988

[54] CHEMICAL COMPOSITION AND USE THEREOF

[75] Inventors: Michael Butters, Farnborough; Barry Nay, Woking, both of England; Keith Smith, Swansea, Wales

[73] Assignee: British Petroleum Company p.l.c., London, England

[21] Appl. No.: 34,747

[22] Filed: Apr. 6, 1987

[30] Foreign Application Priority Data

Apr. 9, 1986 [GB] United Kingdom ................. 8523874

[51] Int. Cl.⁴ ............................................. C07C 39/24
[52] U.S. Cl. ..................................... 568/779; 568/774
[58] Field of Search ............................... 568/774, 779

[56] References Cited

FOREIGN PATENT DOCUMENTS 3318791 12/1983 Fed. Rep. of Germany ...... 568/779
0220302 3/1985 German Democratic Rep. .................................... 568/779
2155009 9/1985 United Kingdom ............... 568/779
2165244 4/1986 United Kingdom ............... 568/779

OTHER PUBLICATIONS

Yaroslavsky, "Tetrahedron Letters", No. 38, pp. 3395-3396 (1974).
Kathawaia et al, "Chemical Abstracts", vol. 54, p. 9812 (1960).

Primary Examiner—Werren B. Lone
Attorney, Agent, or Firm—Brooks Haidt Haffner & Delahunty

[57] ABSTRACT

This invention relates to novel compositions comprising a N-halodialkylamine as defined in the specification and an inorganic oxide. The compositions are useful as halogenating agents for phenolic compounds. The compositions have the advantage that they are milder halogenating agents than halogens or hydrogen halides.

5 Claims, No Drawings

CHEMICAL COMPOSITION AND USE THEREOF

The present invention relates to inorganic oxide derived compositions and to their use as halogenating agents for organic compounds, especially phenolic compounds.

Chlorinated phenols, for example, are valuable industrial products having a variety of uses, which include their use as intermediates in the manufacture of dyestuffs, preservatives, disinfectants, germicides, insecticides and antifungal agents.

Chlorinations of phenolic compounds have been carried out with a variety of chlorinating agents, catalysts and reaction conditions too numerous to mention in detail. Thus chlorophenols are obtained with chlorinating agents such as chlorine, chlorine oxide, $SO_2Cl_2$, NaOCl, tertiary butyl hypochlorite etc. The ortho/para ratio is very dependent upon the nature of the chlorinating agents and the conditions. For example, the chlorination of phenol with tertiary butyl hypochlorite in $CCl_4$ gives an ortho:para ratio of 1.04 (cf. D. R. Harvey and R. O. C. Norman, *J. Chem. Soc.*, 1961, 3604) and this ratio also depends on the concentration of phenol (cf. W. D. Watson, *J. Org. Chem.*, 1974, 39, 1160). Likewise, the chlorination of phenol with Chlorine in $CCl_4$ gives an ortho:para ratio of 2.85 (cf. Y. Ogata et al, *J. Chem. Soc. Perkin Trans II.*, 1984, 451).

We have recently described in our published UK Patent Specification No. 2155009, the use of novel halogenation compositions comprising an inorganic solid and one or more organic halogen-containing compounds, which halogenate aromatic substrates such as toluene under mild conditions and avoid the use of corrosive halogen or hydrogen halide.

We have now found that compositions containing an N-halodialkylamine compound (cf. J. R. Lindsay Smith and L. C. McKeer, *Tet. Letters*, 1983, 3117), such as for example N-chloropiperidine, and an inorganic oxide, such as for example silica gel, alumina or an aluminosilicate are highly effective halogenating agents and are especially useful for the halogenation of phenolic compounds.

Accordingly, the present invention provides a composition for use as a halogenating agent which comprises at least one N-halodialkylamine and at least one inorganic oxide.

By the term 'N-halodialkylamine' is meant here and throughout the specification that the nitrogen atom in the compound is linked directly to (a) at least two separate hydrocarbyl units which may themselves be substituted by other groups and/or which may together form a heterocyclic ring with the nitrogen being the hetero atom, and (b) a halogen atom.

A wide range of N-halodialkylamines may be employed including iodine-containing compounds, although chlorine- and bromine-containing compounds are preferred. Typical of the N-halodialkylamines which may be used in the composition of the present invention are N-chloropiperidine, N-chlorodiisopropylamine, N-chloromorpholine, N,N-dichloropiperazine, N-chlorobis(2-methoxyethyl)amine, N-chlorobis(2-chloroethyl)amine and N-chlorodiethylamine. It should be noted that N-chlorobis-(2-methoxyethyl)amine and N-chlorobis(2-chloroethyl)amine may have explosive properties when in their neat state and they should be handled with care. They may be handled with safety in the form of solutions or suspensions in appropriate solvents. These can be prepared in situ by reacting in aqueous solution the parent dialkylamines, e.g. bis(2-methoxyethyl)amine and bis(2-chloroethyl)amine respectively with sodium hyprochlorite. For further details on the preparation of N-halodialkylamines, the reader is referred to *J. Am. Chem. Soc.*, 1933, 55, 3001 by G. H. Coleman and *Can. J. Chem.*, 1970, 48, 546 by K. U. Ingold. The aqueous reaction mixture may then be stirred in carbon tetrachloride dichloromethane or hydrocarbon solvents so as to extract the N-halodialkylamine directly into the organic solvent of choice.

The inorganic oxides which may be employed include one or more of silica, alumina, silica/alumina, titania, zirconia and both natural and synthetic aluminosilicates.

In the compositions of the present invention the amount of N-halodialkylamine to inorganic oxide may vary over a wide range. The rate of halogenation reaction will vary with the relative proportion of the two components. Typically, the composition may contain 0.2 to 10 moles, preferably 0.5 to 5 moles of the N-halodialkylamine per kilogram of the inorganic oxide.

For example, in the case of a commercial silica (e.g. ex-British Drug Houses) a maximum rate of halogenation is achieved when using 0.65 mole of the N-halodialkylamine per kilogram of the silica.

The halogentating properties of the resulting compositions are quite different from those of the individual components. Many of the compositions falling within the scope of the invention will also tolerate the presence of water.

Such compositions are not only halogenating agents but also have the added advantage of preferentially forming the orthohalogenated isomer in the product during halogenation of phenols. Thus, for example chlorination of 2-methylphenol in carbon tetrachloride at 25° C. with a slight excess of N-chlorobis(2-chloroethyl)amine can give a 94% yield of chloro-2-methylphenols in the proportions 6-chloro-2methylphenol (81%), 4-chloro-2-methylphenol (10%), 2,4-dichloro-2methylphenol (9%) [ratio of ortho substituted: para substituted=8:1]. Chlorination of phenol under the same conditions as above gives an ortho:para ratio of about 15:1. Ortho:para ratios in the product may be varied by varying the phenolic reactant to halogenating agent ratios, the concentration of the reactant(s), the reaction medium, e.g. solvent or the reaction conditions.

Although the compositions are especially useful for the halogenation of simple or substituted phenols e.g. phenol, ortho-chlorophenol, para-chlorophenol, ortho-cresol and meta-cresol, they may also be used for the halogenation of other organic compounds, for example other aromatic compounds.

The components in the composition may be used as a performed physical admixture or may be added sequentially to the halogenation reaction.

The relative proportions of the halogenating composition and the phenolic compound may be varied over a wide range depending on the level of chlorination required. However, molar ratios of the phenolic compound:N-halodialkylamine in the range 3:1 to 1:3 are preferred.

The halogenation reactions may be carried out over a range of temperatures, typically 0°–80° C., but are most conveniently carried out at 15°–40° C. Similarly, the most convenient pressure is atmospheric pressure, but sub-atmospheric or elevated pressures may be employed.

Although the reactions are conveniently carried out in the presence of a solvent, this is not essential. The N-halodialkylamine may initially be deposited on the inorganic solid (with removal of any solvent employed for this purpose), and the reactant may be brought into contact with the supported halogenating agent in a gas flow, as a neat liquid or in solution. Solid-phase reactions are also possible.

The invention will now be further illustrated by reference to the following Examples.

EXAMPLE 1

Silica (3 g, 60–120 BSS mesh), carbon tetrachloride (10 ml), phenol (2.5 mmol) and N-chlorobis(2-chloroethyl)amine (2.63 mmol) were gently stirred together at 25° C. for 24 hours. The reaction mixture was filtered and the solid was washed with a little extra carbon tetrachloride and some methanol to give a filtrate containing ortho-chlorophenol (47%), 2,6-dichlorophenol (10%), 2,4-dichlorophenol (5%), para-chlorophenol (3%) and unreacted phenol (34%), as estimated by gas chromatography.

EXAMPLE 2

The proceduure of Example 1 was repeated except that the reactant was p-chlorophenol instead of phenol. The filtrate obtained contained 2,4-dichlorophenol (55%), 2,4,6-trichlorophenol (16%) and unreacted para-chlorophenol (29%), as estimated by gas chromatography.

EXAMPLE 3

The procedure of Example 1 was repeated except that ortho-chlorophenol was the reactant (instead of phenol), the reaction period was increased to 48 hours and the reagent used was N-chlorodiethylamine. The filtrate obtained contained 2,6-dichlorophenol (32%), 2,4-dichlorophenol (22%), 2,4,6-trichlorophenol (18%) and unreacted ortho-chlorophenol (28%), as estimated by gas chromatography.

EXAMPLE 4

The procedure of Example 1 was repeated except that the reactant was ortho-chlorophenol (instead of phenol) and the reaction period was increased to 48 hours. The filtrate obtained contained 2,6-dichlorophenol (41%), 2,4-dichlorophenol (8.5%), 2,4,6-trichlorophenol (12.5%) and unreacted ortho-chlorophenol (38%), as estimated by gas chromatography.

EXAMPLE 5

The procedure of Example 1 was repeated except that the reactant was ortho-cresol instead of phenol and the reaction period was increased to 48 hours. The filtrate obtained contained 6-chloro-2-methylphenol (76%), 4-chloro-2-methylphenol (9.5%), 4-6-dichloro-2-methylphenol (8.5%) and unreacted 2-methylphenol (6%), as estimated by gas chromatography.

We claim:

1. A composition for use as a halogenating agent which comprises at least one N-halodialkylamine selected from N-chloropiperidine, N-chlorodiisopropyl amine, N-chloromorpholine, N,N-dichloropiperazine, N-chlorobis(2-methoxyethyl)amine, N-chlorobis(2-chloroethyl)amine and N-chlorodiethyl amine and at least one inorganic oxide selected from silica, alumina, silica/alumina, titania, zirconia, natural aluminosilicates, synthetic aluminosilicates and mixtures thereof.

2. A composition according to any one of the preceding claims wherein the composition contains 0.2 to 10 moles of the N-halodialkylamine per kilogram of the inorganic oxide.

3. A process for the halogenation of phenols said process comprising reacting at a temperature between about 0° and 80° C. phenol or a substituted phenol with a composition comprising at least one N-halodialkylamine selected from N-chloropiperidine, N-chlorodiisopropyl amine, N-chloromorpholine, N,N-dichloropiperazine, n-chlorobis(2-methoxyethyl) amine, N-chlorobis(2-chloroethyl) amine and N-chlorodiethyl amine and at least one inorganic oxide selected from silica, alumina, silica/alumina, titania, zirconia, natural aluminosilicates, synthetic aluminosilicates and mixtures thereof.

4. A process according to claim 3 wherein the reactant phenol is selected from phenol, ortho-chlorophenol, para-chlorophenol, ortho-cresol and meta-cresol.

5. A process according to claim 3 or 4 wherein the molar ratio of the phenolic compound to N-halodialkylamine is in the range 3:1 to 1:3.

* * * * *

UNITED STATES PATENT AND TRADEMARK OFFICE
CERTIFICATE OF CORRECTION

PATENT NO. : 4,754,080

DATED : June 28, 1988

INVENTOR(S) : Michael Butters et al

It is certified that error appears in the above-identified patent and that said Letters Patent is hereby corrected as shown below:

Col. 2, line 42 ... "ortho" ... and ... "para"... should be underlined.

Col. 2, line 57, change "performed" to read ... preformed...

Col. 3, lines 21 and 22 ... "ortho" ... and ..."para"... should be underlined.

Col. 3, line 27, correct the spelling of ... "procedure".

Claim 3, line 7, change "n-chlorobis(2-methoxyethyl) amine" to ...N-chlorobis (2-methoxyethyl) amine.

Signed and Sealed this

Twenty-ninth Day of November, 1988

*Attest:*

DONALD J. QUIGG

*Attesting Officer*      *Commissioner of Patents and Trademarks*